United States Patent
Hu et al.

(10) Patent No.: US 12,108,975 B2
(45) Date of Patent: Oct. 8, 2024

(54) MULTIFUNCTIONAL HIGH-FREQUENCY ELECTRIC KNIFE

(71) Applicants: MICRO-TECH (NANJING) CO., LTD., Nanjing (CN); SICHUAN PROVINCIAL PEOPLE'S HOSPITAL, Chengdu (CN)

(72) Inventors: Xiao Hu, Chengdu (CN); Zhi Tang, Nanjing (CN); Mingqiao Fan, Nanjing (CN); Huan Xie, Nanjing (CN); Changqing Li, Nanjing (CN); Derong Leng, Nanjing (CN)

(73) Assignees: MICRO-TECH (NANJING) CO., LTD., Nanjing (CN); SICHUAN PROVINCIAL PEOPLE'S HOSPITAL, Chengdu (CN)

( * ) Notice: Subject to any disclaimer, the term of this patent is extended or adjusted under 35 U.S.C. 154(b) by 1028 days.

(21) Appl. No.: 17/048,240

(22) PCT Filed: Apr. 19, 2019

(86) PCT No.: PCT/CN2019/083463
§ 371 (c)(1),
(2) Date: Oct. 16, 2020

(87) PCT Pub. No.: WO2019/206042
PCT Pub. Date: Oct. 31, 2019

(65) Prior Publication Data
US 2021/0077179 A1    Mar. 18, 2021

(30) Foreign Application Priority Data
Apr. 23, 2018 (CN) .......................... 201810366219.1

(51) Int. Cl.
*A61B 18/14* (2006.01)
*A61B 18/00* (2006.01)

(52) U.S. Cl.
CPC ...... *A61B 18/1445* (2013.01); *A61B 18/1482* (2013.01); *A61B 2018/00107* (2013.01);
(Continued)

(58) Field of Classification Search
None
See application file for complete search history.

(56) References Cited

U.S. PATENT DOCUMENTS 5,820,630 A * 10/1998 Lind ...................... A61B 10/06
606/208
6,156,009 A * 12/2000 Grabek .................. A61B 17/29
604/93.01
(Continued)

FOREIGN PATENT DOCUMENTS

CN    102379739 A    3/2012
CN    103110457 A    5/2013
(Continued)

OTHER PUBLICATIONS

International Search Report dated Jul. 4, 2019 for corresponding International Application No. PCT/CN2019/083463, filed Apr. 19, 2019, 5 pages.
(Continued)

*Primary Examiner* — Ronald Hupczey, Jr.
(74) *Attorney, Agent, or Firm* — Westman, Champlin & Koehler P.A.

(57) ABSTRACT

Provided is a multifunctional high-frequency electric knife, comprising processing portion, sheath portion, and operating portion. The processing portion is provided with an electrode and a clip component; the electrode is provided with a hollow tubular portion; the electrode can be pushed out or retracted relative to far end of the sheath portion; the clip component can be pushed out or retracted relative to far end of the sheath portion; the sheath portion is disposed at
(Continued)

near end of the processing portion and comprises a hollow pull rod and a spring tube; and the operating part is located at near end of the sheath portion and comprises a high-frequency joint connected to the electrode by wire, a component driving, by operating line, the electrode to move, a member driving the hollow pull rod to move, and a liquid inlet allowing liquid to flow to the hollow tubular portion of the electrode.

15 Claims, 7 Drawing Sheets

(52) U.S. Cl.
CPC .............. *A61B 2018/00607* (2013.01); *A61B 2018/0091* (2013.01); *A61B 2018/1412* (2013.01); *A61B 2018/1422* (2013.01); *A61B 2218/002* (2013.01)

(56) References Cited

U.S. PATENT DOCUMENTS

| | | | |
|---|---|---|---|
| 6,190,386 B1* | 2/2001 | Rydell | A61B 18/1442 606/50 |
| 9,138,283 B2 | 9/2015 | Wake | |
| 10,765,804 B2 | 9/2020 | Sohn et al. | |
| 2010/0217151 A1 | 8/2010 | Gostout et al. | |
| 2013/0172885 A1 | 7/2013 | Ichikawa et al. | |
| 2014/0207134 A1 | 7/2014 | Wake | |
| 2016/0256624 A1 | 9/2016 | Sohn et al. | |
| 2019/0374242 A1 | 12/2019 | Avigal et al. | |

FOREIGN PATENT DOCUMENTS

| | | |
|---|---|---|
| CN | 103750901 A | 4/2014 |
| CN | 104248461 A | 12/2014 |
| CN | 104411265 A | 3/2015 |
| CN | 205054424 U | 3/2016 |
| CN | 105636621 A | 6/2016 |
| CN | 106491176 A | 3/2017 |
| CN | 206044658 U | 3/2017 |
| CN | 107343815 A | 11/2017 |
| CN | 107693110 A | 2/2018 |
| CN | 108523985 A | 9/2018 |
| DE | 102011000964 A1 | 6/2012 |
| JP | 2000245740 A | 9/2000 |
| JP | 2001095812 A | 4/2001 |
| JP | 2005237574 A | 9/2005 |
| JP | 2009533109 A | 9/2009 |
| JP | 2011218182 A | 11/2011 |
| JP | 2013111308 A | 6/2013 |
| JP | 2017123995 A | 7/2017 |
| WO | 2011089717 A1 | 7/2011 |
| WO | 2015053365 A1 | 4/2015 |
| WO | 2017042791 A2 | 3/2017 |
| WO | 2017101625 A1 | 6/2017 |
| WO | 2017122607 A1 | 7/2017 |

OTHER PUBLICATIONS

Written Opinion of the International Searching Authority dated Jul. 4, 2019 for corresponding International Application No. PCT/CN2019/083463, filed Apr. 19, 2019, 4 pages.
Decision to Grant Patent dated Mar. 10, 2023, for corresponding CA Patent Application No. 3097932, filed Apr. 19, 2019.
Decision to Grant Patent dated Dec. 2, 2021, for corresponding EP Patent Application No. 19791969.9, filed Apr. 19, 2019.
Decision to Grant Patent dated Apr. 1, 2022, for corresponding JP Patent Application No. 2020-570623, filed Apr. 19, 2019.
Search Report dated May 28, 2021, for corresponding EP Patent Application No. 19791969.9, filed Apr. 19, 2019.
Search Report dated Apr. 23, 2018, for corresponding CN Priority Patent Application No. CN2018/10366219.1, filed Apr. 23, 2018.
Notice of acceptance for patent application dated Dec. 1, 2021, for corresponding AU Patent Application No. 2019260152, filed Apr. 19, 2019.
Office Action dated Sep. 9, 2021, for corresponding AU Patent Application No. 2019260152, filed Apr. 19, 2019.
Office Action dated Oct. 20, 2021, for corresponding CA Patent Application No. 3097932, filed Apr. 19, 2019.
Office Action dated Jul. 29, 2021, for corresponding JP Patent Application No. 2020-570623, filed Apr. 19, 2019.
Office Action dated May 27, 2022. for corresponding KR Patent Application No. 10-2020-7029757, filed Oct. 16, 2020.
Office Action dated Nov. 14, 2023, for corresponding CN Priority Patent Application No. CN2018/10366219.1, filed Apr. 23, 2018.
Notice of Final Rejection dated Dec. 23, 2022, for corresponding KR Patent Application No. 10-2020-7029757, filed Oct. 16, 2022.
Written Opinion of the International Searching Authority dated Jul. 4, 2019 in priority application PCT/CN2019/083463, filed Apr. 19, 2019.

* cited by examiner

MULTIFUNCTIONAL HIGH-FREQUENCY ELECTRIC KNIFE

CROSS-REFERENCE TO RELATED APPLICATION

This Application is a Section 371 National Stage Application of International Application No. PCT/CN2019/083463, filed 19 Apr. 2019, and published as WO 2019/206042 A1 on 31 Oct. 2019, in Chinese, which claims priority to Chinese Patent Application No. 201810366219.1, filed on 23 Apr. 2018, the contents of which are hereby incorporated by reference in their entirety.

TECHNICAL FIELD

The present disclosure relates to an electrosurgical knife (electric knife) for cutting lesioned tissue at high frequency under the guidance of an endoscope in the field of medical instruments, and in particular to a high-frequency electrosurgical knife into which cutting, injection, and hemostasis functions are integrated.

BACKGROUND ART

For over 50 years since the advent of endoscopic technology, the endoscopic technology has gone through the stage from use in disease diagnosis to use in disease therapy, and it has been very effective and reliable for therapy of some digestive diseases and has even become the first therapeutic choice. In recent years, with the development of the endoscopic technology, endoscopic tissue biopsy, endoscopic mucosal resection (EMR), and endoscopic submucosal dissection (ESD) have been widely used and are gradually becoming the preferred therapeutic means for the therapy of gastrointestinal bleeding, polypectomy, and early cancer. Among them, especially ESD has played a key role in the detection, diagnosis, and resection of early cancers.

The endoscopic submucosal dissection refers to an endoscopic minimally invasive technique for submucosal dissection of a lesion larger than 2 cm using a high-frequency instrument. This technique enables the complete resection of a larger lesion and provides accurate pathological diagnosis and staging for the lesion. Compared with traditional surgical procedures, ESD can effect a radical cure of tumors and furthermore maintain a better physiological function in the digestive tract and significantly improve the quality of life of the patient after surgery, which, at present, has become the preferred therapeutic method for early cancers and precancerous lesions of the digestive tract including esophagus.

ESD requires a long time and has a high risk of complications such as bleeding and perforation, because a large area of mucosa will be excised. The current various incision knives for use in endoscopic submucosal dissection generally only have the function of cutting tissue, and rarely have the function of electrocoagulation and hemostasis. Once bleeding occurs, the incision knife must be removed from the channel of the endoscope and replaced with an electrocoagulation forceps for electrocoagulation and hemostasis. Especially for a patient in which abundant blood is supplied to the submucosa, it is necessary to change instruments repeatedly, which greatly increases the surgery operation time, and sometimes may also miss the best time point to perform hemostasis, leading to excessive blood loss and some unnecessary damage to surrounding tissue in the patient. In addition, the ESD procedure is complicated, generally requires a long time, and should be performed under the guidance of an endoscope. The endoscope is first introduced into the human body to find the lesioned tissue. An instrument is introduced into the human body through the channel of the endoscope for marking the lesion. After the lesion is marked, the instrument is withdrawn and replaced with an injection needle for submucosal injection. After the injection, surgery is performed using a suitable electrosurgical knife. It takes about 1 to 2 hours to successfully excise an early cancerous lesion of about 3 cm and extract a specimen for pathological analysis. It is necessary to change instruments in the surgery, which results in more complicated surgery and prolonged surgery time, thereby causing pain to the patient. Therefore, there is a need to develop a high-frequency electrosurgical knife into which cutting, injection, and coagulation functions are integrated.

SUMMARY

An object of the present disclosure is to provide a multifunctional high-frequency electrosurgical knife device, which is capable of cutting lesioned tissue in a human body, coagulating the lesioned tissue at high frequency, cauterizing the lesioned tissue at high temperature, and injecting a liquid into the lesioned tissue, so as to achieve a positionable multifunctional high-frequency electrosurgical knife into which cutting, liquid injection, and coagulation functions are integrated.

Hereinafter, one end of a treatment part is defined as a distal end, and one end of an operating part is defined as a proximal end.

A multifunctional high-frequency electrosurgical knife comprises: a treatment part, a sheath part, and an operating part. The treatment part is located at a distal end of the multifunctional high-frequency electrosurgical knife and comprises: an electrode for cutting tissue and injecting a liquid, which can be pushed out or retracted relative to the distal end of the sheath part and which has a hollow tubular portion extending in an axial direction; and a clip component for performing hemostasis of tissue, which can be pushed out or retracted relative to the distal end of the sheath part and which comprises a first clamping element, a second clamping element, and a first pin shaft by which the first clamping element and the second clamping element are connected, wherein the clip component can be opened and closed by driving the first pin shaft. The sheath part is located at a proximal end of the treatment part and comprises: a hollow pull rod, wherein the electrode may extend distally from its proximal end through the interior of the proximal end of the hollow pull rod, the hollow pull rod is connected to the first clamping element and the second clamping element by means of the first pin shaft, and the hollow pull rod is operable to drive the clip component to be pushed out or retracted relative to the distal end of the sheath part; and an insulating outer tube having a lumen extending along an axis of the sheath part, in which the hollow pull rod and the clip component can be accommodated. When the clip component is in an opened state, the first clamping element and the second clamping element intersect in a cross shape, and the first clamping element and the second clamping element are symmetrically shaped, so as to form a clip portion of the clip component. A locking member is provided on an outer surface of the hollow tubular portion of the electrode, a limit block is provided on an outer wall of the hollow tubular portion of the electrode, and a maximum distance by which the electrode is protruded distally can be controlled by cooperation of the limit block with the first pin shaft. When the first clamping element and the second clamping element are closed, the locking member is locked by the first clamping element and the second clamping element to control a minimum distance by which the electrode is protruded distally. The operating part is located at the proximal end of the sheath part and comprises: a high-frequency connector connected to the electrode via a wire; a component that drives the electrode to move by means of an operating wire; a member that drives the hollow pull rod to move; and a liquid inlet that allows a liquid to flow to the hollow tubular portion of the electrode.

Preferably, the member is a slider, which is slidable back and forth along the core rod, to protrude or retract the clip component.

Preferably, the component that drives the electrode to move is a thumb ring, which is provided at the proximal end of the operating part, and the thumb ring is slidable back and forth along the core rod, to protrude or retract the electrode.

The sheath part further comprises a spring tube, covering an outer layer of the hollow pull rod. An outer surface of the distal end of the hollow pull rod is covered with a fixed base, which is connected to the distal end of the spring tube. The operating part further comprises a core rod, extending along the axial direction of the high-frequency electrosurgical knife, and a distal end of the core rod is connected to the insulating outer tube.

The sheath part is flexible and comprises a fixed base, a hollow pull rod, a spring tube, and an insulating outer tube. The treatment part, which is provided at a position closer to the distal side than the sheath part, comprises: a clip component and an electrode. The operating part, which is provided at the proximal end of the sheath part, is used for operating the treatment part and comprises a high-frequency connector, a slider, a liquid inlet, a thumb ring, and a core rod.

The treatment part has a clip component and an electrode, wherein the clip component comprises: a first clamping element, a second clamping element, a first pin shaft, a second pin shaft, a third pin shaft, a fourth pin shaft, a first jaw arm, a second jaw arm, a third jaw arm, and a fourth jaw arm. The clip component is used for performing hemostasis of tissue. The clip component can be pushed out or retracted relative to the distal end of the sheath part. The clip component comprises a first clamping element and a second clamping element, the first clamping element and the second clamping element are connected by the first pin shaft, and the clip component can be opened and closed by driving the first pin shaft. The hollow pull rod is also movably connected to the third jaw arm and the fourth jaw arm by means of the first pin shaft, the third jaw arm and the first jaw arm are movably connected by the third pin shaft, the fourth jaw arm and the second jaw arm are movably connected by the fourth pin shaft, and the first jaw arm and the second jaw arm are movably connected to the hollow pull rod by means of the second pin shaft. The first clamping element and the second clamping element intersect in a cross shape, the intersecting positions are movably connected by the first pin shaft to form a clip portion of the clip component. The first clamping element and the second clamping element are symmetrically shaped, and the first clamping element and the second clamping element are combined such that any one of a T shape, an L shape, a cylindrical shape, or a spherical shape is formed by their end portions. When the protruding portion of the electrode is in contact with the lesioned tissue, the first clamping element and the second clamping element are in the closed state. The first clamping element and the second clamping element are coated with a coating film or ceramic material, which can serve as an insulator. The first jaw arm and the second jaw arm may also be in a hook structure at their ends, and are movably connected to the first clamping element and the second clamping element by means of the third pin shaft and the fourth pin shaft, respectively. The electrode comprises: a hollow tubular portion extending in an axial direction and a protrusion at the distal end. The distal end of the electrode extends outwardly in a direction perpendicular to an axis of the hollow tubular portion by a length greater than the radius of the cross section of the hollow tubular portion of the electrode, and the outwardly extending portion forms a protrusion at the distal end of the electrode. Preferably, the protrusion has a cross section distributed (arranged) radially, for example, distributed circumferentially, distributed in a triangular shape, or distributed in a Y shape. The protrusion may be in the form of a three-dimensional shape such as a hemisphere, a sphere, a cylinder, a triangular prism, a Y shape, or the like. When the electrode is powered on, the protruding portion can cut the target lesioned tissue, which serves as the head portion of the entire high-frequency electrosurgical knife. Alternatively, the electrode may have only the hollow tubular portion extending in the axial direction, and in this case, the hollow tubular portion serves as the head portion of the entire high-frequency electrosurgical knife. A locking member is provided on the outer wall of the hollow tubular portion of the electrode. The locking member is block-shaped, ring-shaped, or tubular, wherein the block-shaped locking member may consist of a set of locking blocks spaced apart from each other. The electrode is made of a metal material, which is not limited to conductive materials such as stainless steel, titanium, and tungsten. The electrode can be pushed out or retracted and cut the target lesioned tissue when it is pushed out. The hollow tubular portion of the electrode is partially located in the core rod and partially extends from the core rod. The part of the hollow tubular portion of the electrode that extends from the core rod is provided with an insulating outer tube, which is positionally fixed. Here, the hollow tubular portion of the electrode extends from the distal side of the sheath part to the operating part in the axial direction of the sheath part and is connected to the thumb ring of the operating part via an operating wire.

The sheath part is provided at the proximal end of the treatment part and comprises: a fixed base, a hollow pull rod, a spring tube, an insulating outer tube, and a locking member. The insulating outer tube is coated with an insulating coating to serve as an insulator. The insulating outer tube has a lumen extending along the axis of the sheath part, and the locking member is provided on the outer wall of the hollow tubular portion of the electrode in the insulating outer tube. When the locking member is moved to the distal ends of the first clamping element and the second clamping element, which are in the closed state, the locking member is locked by the clamping elements to achieve positioning. At this time, the electrode has a minimum protruded length. A limit block may also be provided on the outer wall of the hollow tubular portion of the electrode as required. The limit block will be locked by the first pin shaft when it is moved toward the distal end of the electrosurgical knife. The maximum distance by which the head of the knife is protruded is controlled by the cooperation of the limit block with the first pin shaft.

The limit block is block-shaped or ring-shaped. The locking member and the limit block may be provided with an insulating coating or insulated by themselves. The limit block may be disposed at a certain distance on the outer wall of the hollow tubular portion of the electrode, so as to reserve a length for the head of the knife, so that the hollow tubular portion and the protrusion of the electrode can be completely received into the insulating outer tube. When the position of the locking member is flush with the distal end of the insulating outer tube, the head of the knife is only partially received in the insulating outer tube. A spiral member coated with an insulating coating or a hollow hose with a conductive layer is used as the spring tube, so that the sheath part is freely bendable in an endoscope and thus can pass through a curve of the endoscope in a better way. The proximal outer layer of the hollow tubular portion of the electrode is covered with a hollow pull rod. The outer layer of the hollow pull rod is covered with a spring tube. The spring tube and the hollow tubular portion of the electrode, serving as a driving part, are components for torque transmission, such that double drive is formed inside the sheath part. Moreover, the proximal end of the spring tube communicates with the hollow tubular portion of the electrode, to achieve a conducting circuit. The distal end of the spring tube is provided with a fixed base, which can connect the pull rod and the distal end of the spring tube.

The operating part has a high-frequency connector, a slider, a liquid inlet, a core rod, and a thumb ring. The core rod extends in the axial direction of the high-frequency electrosurgical knife. The distal end of the core rod is connected to the insulating outer tube. A thumb ring for controlling the movement of the hollow tubular portion of the electrode is provided at the end of the core rod. The thumb ring may be in the shape of a circle, a square, an oval, or the like. The thumb ring is connected to the proximal end of the hollow tubular portion of the electrode. The hollow tubular structure of the electrode has an inner diameter smaller than that of the core rod, so that when the thumb ring is pulled, the hollow tubular portion of the electrode can be pulled back and forth along the interior of the core rod, to pushed out or retract the electrode. The protruded amount of the head of the knife is accurately restricted by abutment of the limit block on the outer wall of the hollow tubular portion against the first pin shaft. In specific operations, in the event of a bend or curve or the like, there is a sufficient length between the electrode and the core rod, to ensure an allowance for the protruded amount of the head of the knife. A slider is provided at the middle of the core rod. When the slider is pushed, the hollow pull rod can reciprocate in the cavity along the core rod to push out or retract the clip component. The diameter dimension of the inner cavity of the core rod is larger than the diameter dimension of the inner cavity of the spring tube, the diameter dimension of the inner cavity of the spring tube is larger than the diameter dimension of the inner cavity of the hollow pull rod, and the diameter dimension of the inner cavity of the hollow pull rod is larger than the diameter dimension of the hollow tubular portion of the electrode, so that it is ensured that the hollow tubular portion of the electrode is coaxially inserted into the interior of the spring tube. A liquid inlet, such as a 6% Luer connector, is also provided at the end of the core rod. A syringe or an infusion pump may be connected to the 6% Luer connector to inject a liquid, such as normal saline or the like. The high-frequency connector is located at the distal end of the operating part. The high-frequency connector is connected to the spring tube inside the electrosurgical knife. The high-frequency connector is connected to an external high-frequency power generator, wherein the high-frequency generator includes, but is not limited to, CONMED 60-8200-230, ERBE VIO300S, 300D, among others.

In an actual operation process, the insulating outer tube may be first moved proximally, and the slider is pushed to move toward the distal end of the high-frequency electrosurgical knife so that the hollow pull rod drives the first clamping element and the second clamping element to move. Thus, the spring tube and the hollow tubular portion of the electrode can drive the first clamping element and the second clamping element to be opened, closed, and rotated, so that the first clamping element and the second clamping element are opened and can be used as a hemostatic forceps for electrocoagulation and hemostasis, and the clip component is freely rotatable to conveniently and accurately grasp a bleeding site. When the hemostasis is completed, the slider is pushed to move toward the proximal end of the high-frequency electrosurgical knife, so that the first clamping element and the second clamping element are closed. The thumb ring is pushed to move toward the distal end of the high-frequency electrosurgical knife, so that the electrode is protruded, and the protrusion of the electrode is used as an incision knife to cut the lesioned tissue. The electrode may only have a hollow tubular portion extending in the axial direction, and the hollow tubular portion is used for cutting the lesioned tissue. When it is necessary to inject a liquid into tissue, the distal end of the electrode may be placed inside the target mucosal tissue, and an infusion pump or an external syringe is connected to the 6% Luer connector to inject normal saline or indigo carmine, so that the mucosal tissue is elevated, and a liquid buffer layer, i.e., a "water cushion", is formed under the mucosa. The "water cushion" allows an effective separation between the muscular layer and the lesioned tissue, and also effectively prevents heat conduction, so that a clearer field of view is provided in surgery, and the risk of bleeding is significantly reduced because blood vessels are squeezed and closed by the water cushion. This liquid channel may also be used for cleaning the bleeding site. There is no need to change parts frequently during the surgical operation, which greatly reduces the surgery time and improves the safety of the surgery.

Advantageous Effects

The multifunctional high-frequency electrosurgical knife according to the present disclosure has an electrode made of a metal material with a hollow tubular portion, so as to form a liquid channel, so that a liquid can pass through the hollow tubular portion of the electrode and can be submucosally injected for elevating mucosal tissue, or can also be used for cleaning a bleeding site.

The multifunctional high-frequency electrosurgical knife according to the present disclosure has a spiral member coated with an insulating coating or a hollow hose with a conductive layer used as the spring tube of the sheath part, so that the electrosurgical knife is freely bendable in an endoscope.

The multifunctional high-frequency electrosurgical knife according to the present disclosure has a first clamping element and a second clamping element that can be freely closed and opened, and the clip component when closed is freely rotatable to conveniently and accurately grasp a bleeding point.

The multifunctional high-frequency electrosurgical knife according to the present disclosure has a locking member and a limit block on the outer surface of the hollow tubular portion of the electrode, so that free positioning can be achieved, and the knife can be selectively protruded at different lengths according to actual conditions.

10, treatment part; 11, electrode; 111, hollow tubular portion; 112, protrusion; 12a, first clamping element; 12b, second clamping element; 13a, first pin shaft; 13b, second pin shaft; 13c, third pin shaft; 13d, fourth pin shaft; 14a, first jaw arm; 14b, second jaw arm; 14c, third jaw arm; 14d, fourth jaw arm; 15, locking member; 16a, hook structure; 16b, hook structure; 17, limit block; 20, sheath part; 21, fixed base; 22, hollow pull rod; 23, spring tube; 24, insulating outer tube; 30, operating part; 31, high-frequency connector; 32, slider; 33, core rod; 34, thumb ring; 35, liquid inlet; 40, lesioned tissue

DETAILED DESCRIPTION OF EMBODIMENTS

In order to further clarify the objects, technical solutions, and advantages of the present disclosure, the present disclosure will be described in further detail with reference to the drawings and embodiments below. It should be understood that the specific embodiments described herein are intended only to explain the present disclosure and are not intended to limit the present disclosure.

Embodiments

Figure 1:
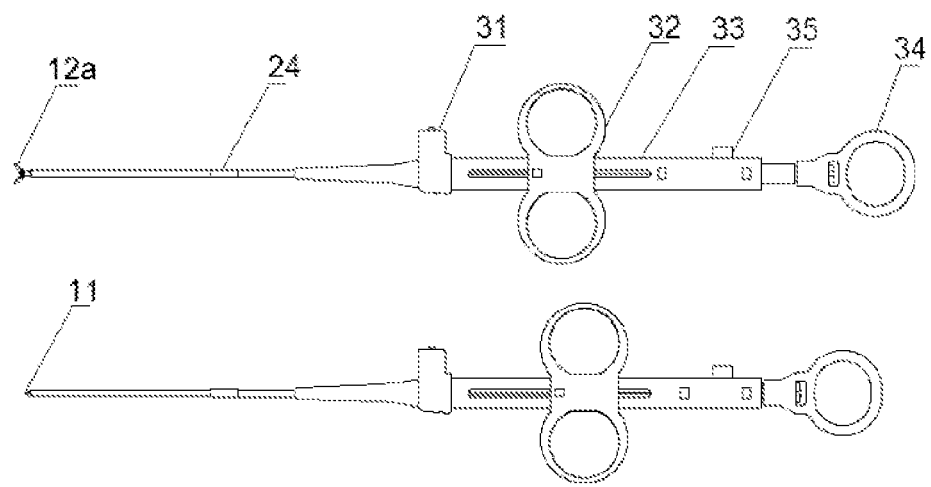
FIG. 1 is a schematic diagram of a multifunctional high-frequency electrosurgical knife.
Figure 2:
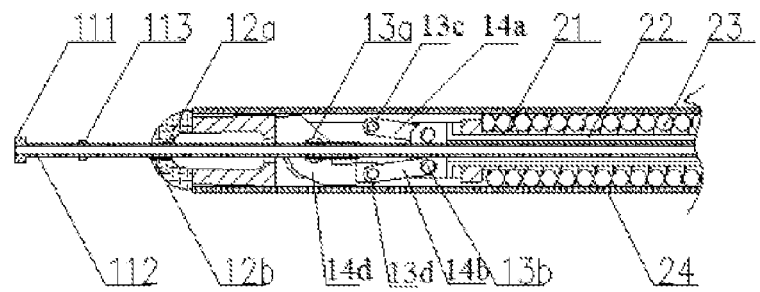
FIG. 2 is a partially enlarged schematic diagram of the multifunctional high-frequency electrosurgical knife in a state where clamping elements are closed.

Hereinafter, one end of the treatment part is defined as a distal end, and one end of the operating part is defined as a proximal end. As shown in FIGS. 1-3, a multifunctional high-frequency electrosurgical knife in this embodiment comprises a treatment part 10, a sheath part 20, and an operating part 30. The treatment part 10 comprises an electrode 11, a clip having a first clamping element 12a and a second clamping element 12b, a first pin shaft 13a, a second pin shaft 13b, a third pin shaft 13c, a fourth pin shaft 13d, a first jaw arm 14a, a second jaw arm 14b, a third jaw arm 14c, and a fourth jaw arm 14d. The first jaw arm 14a and the third jaw arm 14c are movably connected by the third pin shaft 13c, and the second jaw arm 14b and the fourth jaw arm 14d are movably connected by the fourth pin shaft 13d. The first jaw arm 14a and the third jaw arm 14c may also be movably connected in the form of a hook structure 16a, and the second jaw arm 14b and the fourth jaw arm 14d may also be movably connected in the form of a hook structure 16b. The first jaw arm 14a and the second jaw arm 14b are movably connected by the second pin shaft 13b. The third jaw arm 14c and the fourth jaw arm 14d are movably connected to the tails of the first clamping element 12a and the second clamping element 12b by means of the first pin shaft 13a. The first pin shaft 13a is fixedly connected to the distal end of the hollow pull rod 22, and the second pin shaft 13b is movably connected to the distal end of the hollow pull rod 22, so that the hollow pull rod 22 can be pulled to protrude or withdraw the clip component.

Figure 3A:
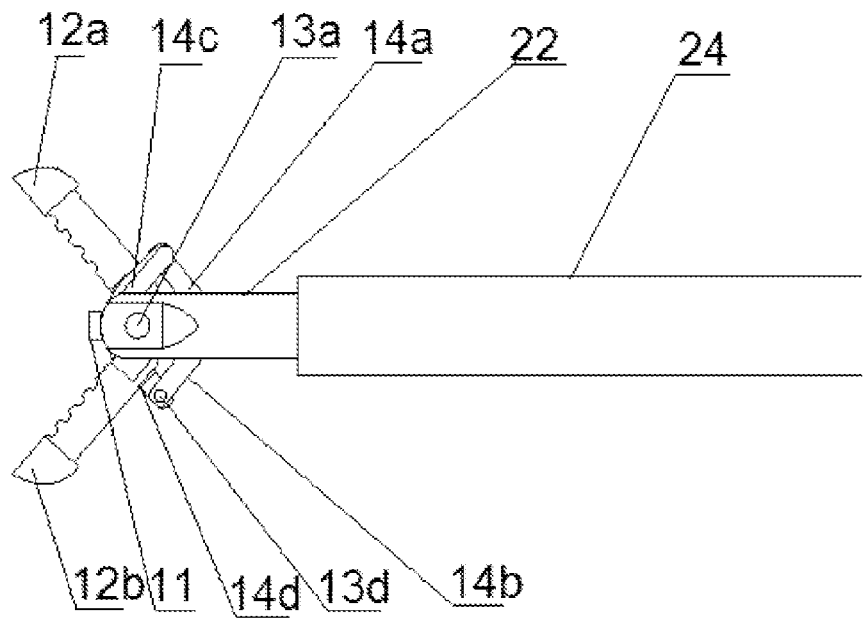
FIGS. 3A-3B are partially enlarged schematic diagrams of the multifunctional high-frequency electrosurgical knife in a state where the clamping elements are opened.
Figure 3B:
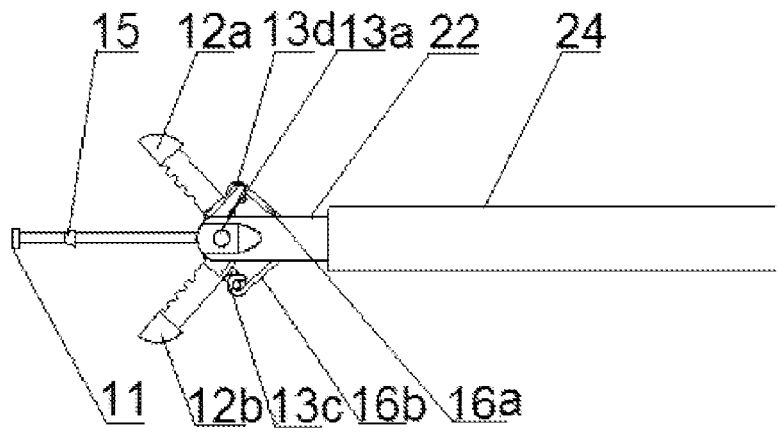

As shown in FIGS. 3A and 3B, the first clamping element 12a and the second clamping element 12b intersect in a cross shape. The clip movably connected by the first pin shaft 13a can be opened or closed. The first clamping element 12a and the second clamping element 12b intersect in a cross shape, in the opened state. The first clamping element 12a and the second clamping element 12b are symmetrically shaped, so as to form a clip portion of the clip component for performing hemostasis of tissue. The first clamping element 12a and the second clamping element 12b may be covered with a coating film or ceramic material serving as an insulator.

As shown in FIGS. 5A-5F, the electrode 11 is passed from the distal end through the hollow pull rod 22 and connected to an operating wire at the proximal end. The electrode 11 may comprise a hollow tubular portion 111 extending in an axial direction and a protrusion 112 at the distal end, or the electrode 11 may have only the hollow tubular portion 111 extending in the axial direction without the protrusion 112. The distal end of the electrode 11 extends outwardly in a direction perpendicular to the axis of the hollow tubular portion 111 by a length greater than the radius of the cross section of the hollow tubular portion 111 of the electrode, and the outwardly extending portion forms a protrusion 112 at the distal end of the electrode 11.

Figure 5A:
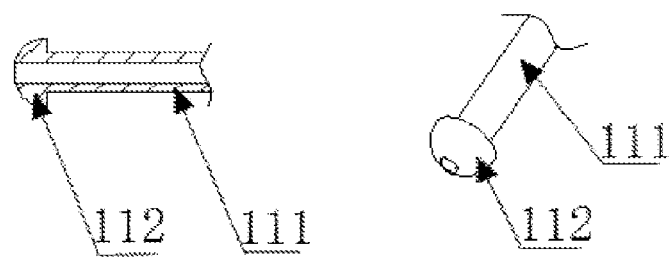
FIGS. 5A-5F are schematic diagrams of a distal end of an electrode.
Figure 5B:
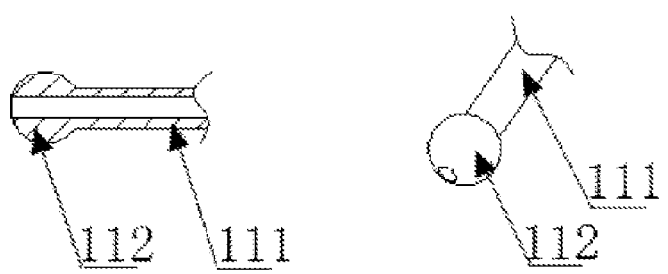
Figure 5C:
Figure 5D:
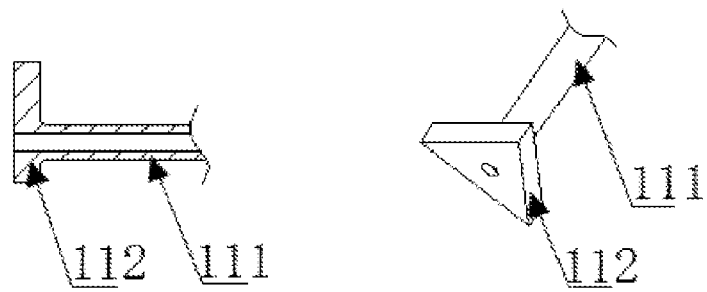
Figure 5F:
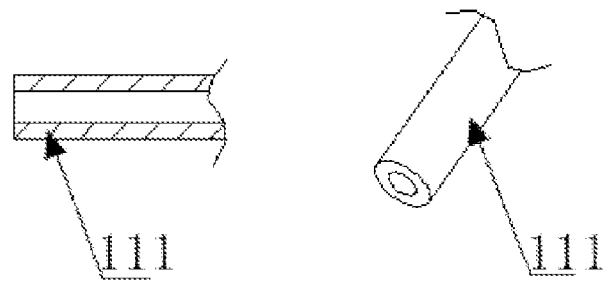
Figure 5E:
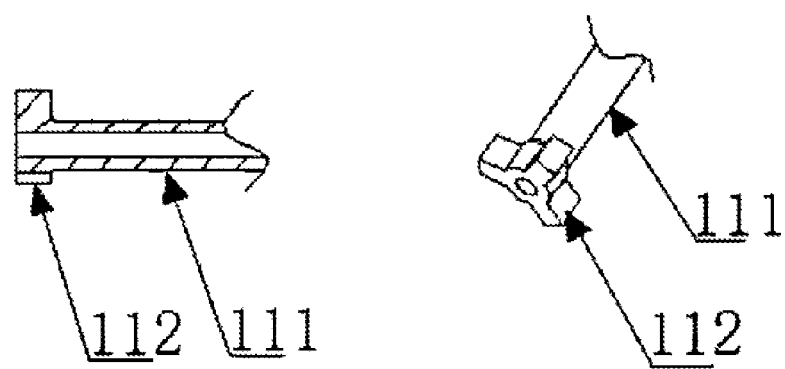

As shown in FIG. 5A, the protrusion 112 has a cross section distributed (arranged) circumferentially, and the protrusion 112 is in the shape of a hemisphere. As shown in FIG. 5B, the protrusion 112 has a cross section distributed (arranged) circumferentially, and the protrusion 112 is in the shape of a sphere. As shown in FIG. 5C, the protrusion 112 has a cross section distributed (arranged) circumferentially, and the protrusion 112 is in a cylindrical shape. As shown in FIG. 5D, the protrusion 112 has a cross section distributed (arranged) in a triangular shape, and the protrusion 112 is in the shape of a triangular prism. As shown in FIG. 5E, the protrusion 112 has a cross section distributed (arranged) in a Y shape, and the protrusion 112 is Y-shaped. As shown in FIG. 5F, the electrode 11 may have only the hollow tubular portion 111 extending in the axial direction.

As shown in FIG. 2, the sheath part 20 comprises a fixed base 21, a hollow pull rod 22, a spring tube 23, an insulating outer tube 24, a locking member 15, and a limit block 17. The hollow pull rod 22 may be a hollow pull rod allowing the electrode 11 to pass through. The first pin shaft 13a is fixedly connected to the distal end of the hollow pull rod 22. The third jaw arm 14c and the fourth jaw arm 14d are movably connected to the tails of the first clamping element 12a and the second clamping element 12b by means of the first pin shaft 13a, and fixed to the hollow pull rod 22. The second pin shaft 13b is movably connected to the distal end of the hollow pull rod 22. The first jaw arm 14a and the second jaw arm 14b are movably connected to each other by means of the second pin shaft 13b, and movably fixed to the hollow pull rod 22. Thus, the hollow pull rod 22 can be pulled to enable the clip component to be protruded or withdrawn. The outer surface of the distal end of the hollow pull rod 22 is covered with the fixed base 21. The fixed base 21 may be connected to the distal end of the spring tube 23. The spring tube 23 can increase the flexibility and bendability of the multifunctional high-frequency electrosurgical knife. The insulating outer tube 24 has a lumen extending along the axis of the sheath part 20, in which the hollow pull rod 22 is movable freely.

Figure 4A:
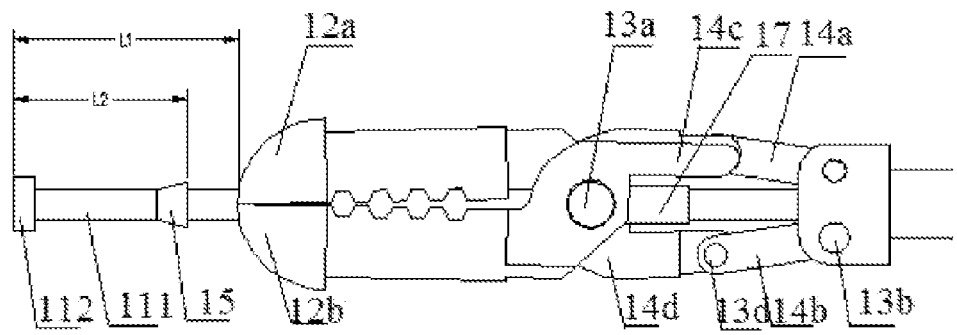
FIGS. 4A-4B are schematic diagrams of the multifunctional high-frequency electrosurgical knife with different protruded lengths of the knife.
Figure 4B:
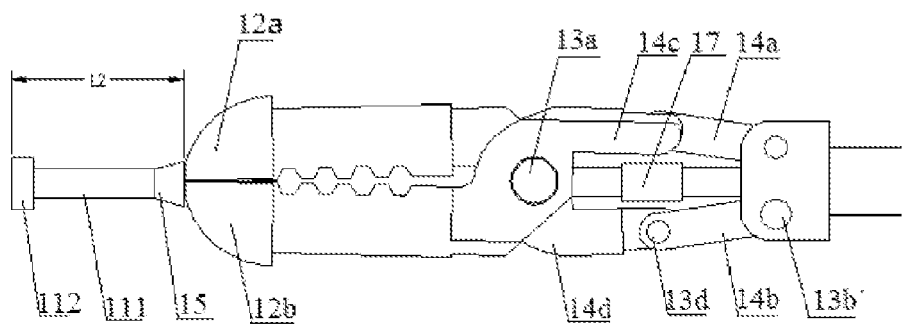

As shown in FIG. 2 and FIGS. 4A-4B, the locking member 15 is provided on the outer surface of the hollow tubular portion 111. The locking member 15 is block-shaped, ring-shaped, or tubular, wherein the block-shaped locking member may consist of a set of locking blocks spaced apart from each other. The limit block 17 is provided on the outer wall of the hollow tubular portion 111 of the electrode. The limit block 17 will be locked by the first pin shaft 13a to control the maximum distance by which the electrode 11 is protruded toward the front end, thereby controlling the protruded length of the electrode 11. When the locking member 15 is moved to the distal ends of the first clamping element 12a and the second clamping element 12b, which are in the closed state, the locking member 15 is locked by the two clamping elements to achieve positioning. At this time, the electrode 11 has a minimum protruded length. The limit block 17 is block-shaped or ring-shaped.

As shown in FIGS. 1 and 2, the operating part 30 is provided at the proximal end of the sheath part 20, which can push out or retract the electrode 11 and the clip component relative to the front end of the sheath part 20, and can provide a lumen through which a liquid is injected. The operating part 30 comprises a high-frequency connector 31, a slider 32, a core rod 33, a thumb ring 34, and a liquid inlet 35. The thumb ring 34 at the proximal end is connected to the electrode 11 via an operating wire, so as to control the protruding and withdrawal of the electrode 11. The high-frequency connector 31 may be connected to the electrode 11 via a wire, to supply the electrode 11 with a high-frequency current. The electrode 11 extends distally from its proximal end through the interior of the proximal end of the hollow pull rod 22. The slider 32 is connected to the proximal end of the hollow pull rod 22, and the slider 32 is movable back and forth along the core rod 33, so as to drive the hollow pull rod 22 to move, for protruding or retracting the clip component. When the slider 32 is pushed forward, the hollow pull rod 22 drives the first clamping element 12a and the second clamping element 12b to be moved distally and gradually opened to intersect in a cross shape. When the slider 32 is retracted backward, the hollow pull rod 22 drives the first clamping element 12a and the second clamping element 12b to be contracted into the insulating outer tube 24. In this way, the opening and closing of the first clamping element 12a and the second clamping element 12b are achieved. The spring tube 23 and the electrode 11, serving as a driving part, are components for torque transmission, so that double drive is formed inside the sheath part 20. The spring tube 23 increases the twisting force for the driving part.

Figure 6A:
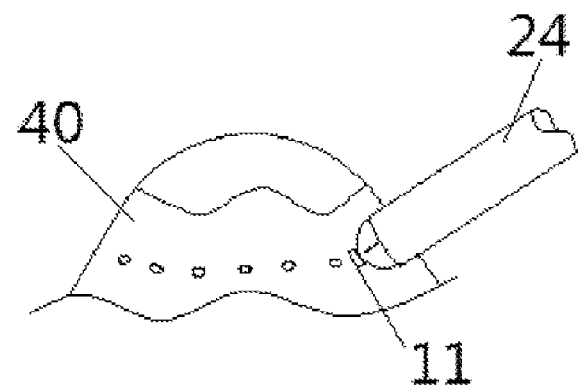
FIGS. 6A-6D are schematic diagrams illustrating a process of using the multifunctional high-frequency electrosurgical knife.

FIGS. 6A-6D illustrate an operation procedure of the multifunctional high-frequency electrosurgical knife in the present disclosure. During an actual operation, as shown in FIG. 6A, the multifunctional high-frequency electrosurgical knife of the present disclosure is inserted to the vicinity of the lesioned tissue 40 through a channel of an endoscope. In this process, the electrode 11 is kept in the retracted state, the protrusion 112 of the electrode is closely attached to the first clamping element 12a and the second clamping element 12b, and the first clamping element 12a and the second clamping element 12b are contracted in the insulating outer tube 24. After the multifunctional high-frequency electrosurgical knife reaches the lesioned tissue 40, the electrode 11 is still kept in the retracted state, and the high-frequency connector 31 of the multifunctional high-frequency electrosurgical knife of the present disclosure is connected to an external high-frequency generator, wherein the high-frequency generator includes, but is not limited to, CONMED 60-8200-230, ERBE VIO300S, 300D, etc. Thus, a high-frequency current is applied to the electrode 11, and the periphery of the lesioned tissue 40 is marked. After the marking is completed, the application of the high-frequency current is stopped.

Figure 6B:
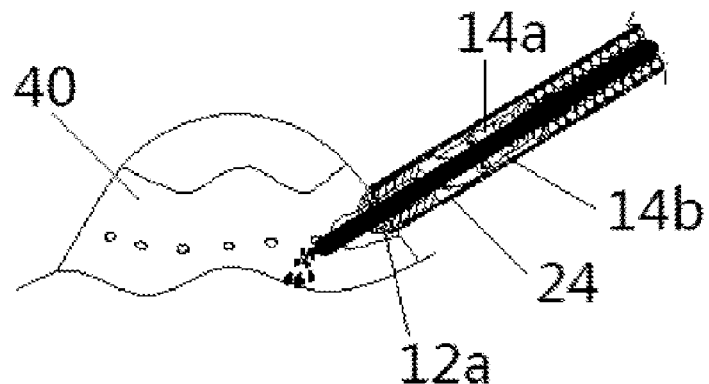

As shown in FIG. 6B, the thumb ring 34 of the multifunctional high-frequency electrosurgical knife of the present disclosure is pushed to move forward, so that the electrode 11 is protruded. The electrode 11 is placed at a marked point and inserted into the submucosa of the lesioned tissue 40, and normal saline or indigo carmine is injected into the lesioned tissue 40 through the liquid inlet 35 so that the tissue is elevated.

Figure 6C:
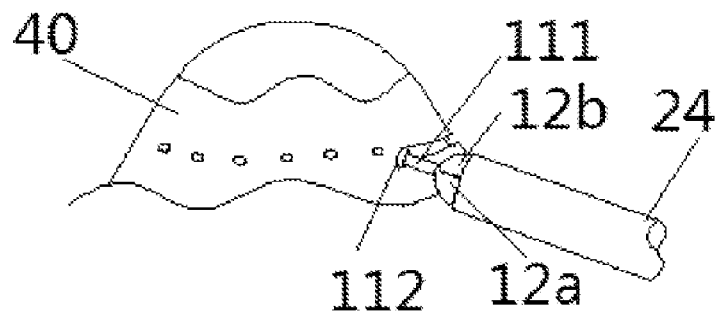
Figure 6D:
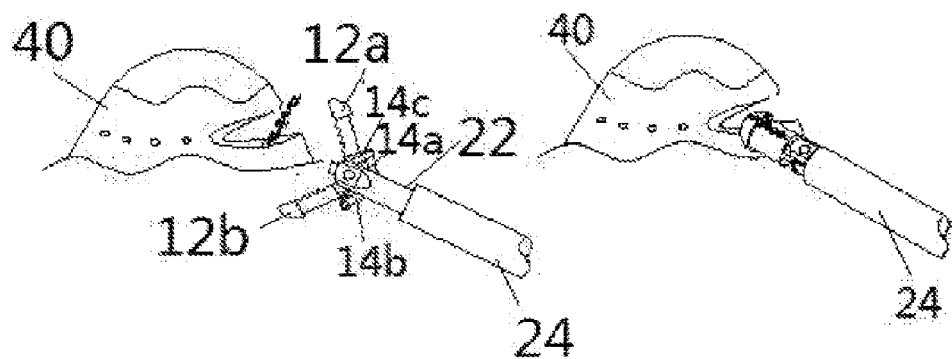

As shown in FIGS. 6C-6D, after the lesioned tissue is elevated, a high-frequency current is applied again to the electrode, while the tissue is cut by the electrode 11 in a direction shown in FIG. 6C. As shown in FIG. 6D, after the cutting is finished, the application of the high-frequency current is stopped, and the slider 32 is pushed forward to drive the hollow pull rod 22 to move forward, so that the clip component is opened, and the first clamping element 12a and the second clamping element 12b are opened to intersect in a cross shape. Then, the thumb ring 34 is retracted backward to withdraw the electrode 11, so that the opened first clamping element 12a and second clamping element 12b can be used as a hemostatic forceps for electrocoagulation and hemostasis. The clip component is rotatable freely to conveniently and accurately grasp a bleeding point.

Figure 7:
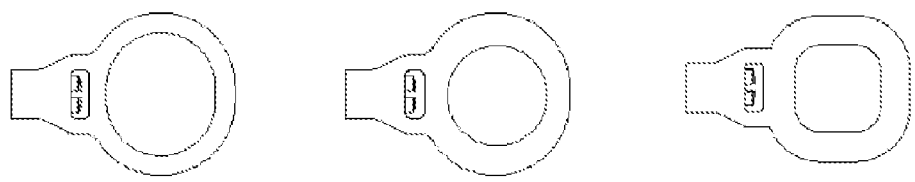
FIG. 7 is a schematic diagram of a thumb ring.

As shown in FIG. 7, the thumb ring may be in a shape of circle, square, oval, or the like.

Four functions can be achieved by using the instrument constructed as described above. Firstly, the multifunctional high-frequency electrosurgical knife according to the present disclosure has both an electrode and a clip component and thus can achieve the integrated functions of liquid injection, cutting, and hemostasis, so that there is no need to frequently change instruments during a surgical procedure, thereby greatly shortening the surgery time and improving the safety of surgery. Secondly, the multifunctional high-frequency electrosurgical knife according to the present disclosure has an electrode made of a metal material with a hollow tubular portion, and the hollow portion forms a liquid channel, so that a liquid can pass through the hollow tubular portion of the electrode and can be submucosally injected for elevating mucosal tissue, or can also be used for cleaning a bleeding site. Thirdly, a spiral member coated with an insulating coating or a hollow hose with a conductive layer is used as the spring tube of the sheath part, so that the electrosurgical knife is freely bendable in an endoscope. Fourthly, the multifunctional high-frequency electrosurgical knife according to the present disclosure has a first clamping element and a second clamping element that can be freely closed and opened, and a torsional force from the spring tube is transmitted to the clip component so that the clip component is freely rotatable to conveniently and accurately grasp a bleeding point. Fifthly, the multifunctional high-frequency electrosurgical knife according to the present disclosure has a locking member and a limit block on the hollow tubular portion of the electrode, so that free positioning can be achieved, and the electrode can be selectively protruded at different lengths according to actual conditions.

The above description is only illustrative of preferable embodiments of the present disclosure to enable those skilled in the art to understand or implement the invention of the present disclosure. Various modifications and combinations of these embodiments will be apparent to those skilled in the art. The general principles defined herein can be implemented in other embodiments without departing from the spirit or scope of the present disclosure. Therefore, the present disclosure will not be limited to these embodiments shown herein, but should conform to the widest scope consistent with the principles and novel features disclosed herein.

What is claimed is:

1. A multifunctional high-frequency electrosurgical knife, comprising:
a treatment part, a sheath part, and an operating part,
wherein the treatment part is located at a distal end of the multifunctional high-frequency electrosurgical knife and comprises: an electrode, configured to cut a tissue and inject a liquid, wherein the electrode is able to be pushed out or retracted relative to a distal end of the sheath part and the electrode has a hollow tubular portion extending in an axial direction; and a clip component, configured to perform hemostasis of a tissue, wherein the clip component is able to be pushed out or retracted relative to the distal end of the sheath part and the clip component comprises a first clamping element, a second clamping element, and a first pin shaft by which the first clamping element and the second clamping element are connected, wherein the clip component is able to be opened and closed by the first pin shaft being driven;
the sheath part is located at a proximal end of the treatment part and comprises: a hollow pull rod, wherein the electrode is able to extend distally from its proximal end through an interior of a proximal end of the hollow pull rod, the hollow pull rod is connected to the first clamping element and the second clamping element by means of the first pin shaft, and the hollow pull rod is operable to drive the clip component to be pushed out or retracted relative to the distal end of the sheath part; and an insulating outer tube, having a lumen extending along an axis of the sheath part, in which the hollow pull rod and the clip component are accommodated, wherein the sheath part further comprises a spring tube, which covers an outer layer of the hollow pull rod; and
the operating part is located at a proximal end of the sheath part and comprises: a high-frequency connector, connected to the electrode via a wire; a component, driving the electrode to move by means of an operating wire; a member, driving the hollow pull rod to move; and a liquid inlet, allowing a liquid to flow to the hollow tubular portion of the electrode.

2. The multifunctional high-frequency electrosurgical knife according to claim 1, wherein a distal end of the electrode extends outwardly in a direction perpendicular to an axis of the hollow tubular portion by a length greater than a radius of a cross section of the hollow tubular portion of the electrode, and an outwardly extending portion forms a protrusion at the distal end of the electrode.

3. The multifunctional high-frequency electrosurgical knife according to claim 2, wherein the protrusion has a cross section arranged radially.

4. The multifunctional high-frequency electrosurgical knife according to claim 1, wherein an outer surface of a distal end of the hollow pull rod is covered with a fixed base, wherein the fixed base is connected to a distal end of the spring tube.

5. The multifunctional high-frequency electrosurgical knife according to claim 1, wherein when the clip component is in an opened state, the first clamping element and the second clamping element intersect in a cross shape, and the first clamping element and the second clamping element are symmetrically shaped, so as to form a clip portion of the clip component.

6. The multifunctional high-frequency electrosurgical knife according to claim 1, wherein the first clamping element and the second clamping element are coated with a coating film or ceramic material.

7. The multifunctional high-frequency electrosurgical knife according to claim 1, wherein the operating part further comprises a core rod, which extends along an axial direction of the high-frequency electrosurgical knife, and a distal end of the core rod is connected to the insulating outer tube.

8. The multifunctional high-frequency electrosurgical knife according to claim 7, wherein the member is a slider, wherein the slider is slidable back and forth along the core rod, so as to protrude or retract the clip component.

9. The multifunctional high-frequency electrosurgical knife according to claim 1, wherein the component, driving the electrode to move, is a thumb ring provided at a proximal end of the operating part, wherein the thumb ring is slidable back and forth along the core rod, so as to protrude or retract the electrode.

10. A multifunctional high-frequency electrosurgical knife comprising:
a treatment part, a sheath part, and an operating part,
wherein the treatment part is located at a distal end of the multifunctional high-frequency electrosurgical knife and comprises: an electrode, configured to cut a tissue and inject a liquid, wherein the electrode is able to be pushed out or retracted relative to a distal end of the sheath part and the electrode has a hollow tubular portion extending in an axial direction; and a clip component configured to perform hemostasis of a tissue, wherein the clip component is able to be pushed out or retracted relative to the distal end of the sheath part and the clip component comprises a first clamping element, a second clamping element, and a first pin shaft by which the first clamping element and the second clamping element are connected, wherein the clip component is able to be opened and closed by the first pin shaft being driven;
the sheath part is located at a proximal end of the treatment part and comprises: a hollow pull rod, wherein the electrode is able to extend distally from its proximal end through an interior of a proximal end of the hollow pull rod, the hollow pull rod is connected to the first clamping element and the second clamping element by means of the first pin shaft, and the hollow pull rod is operable to drive the clip component to be pushed out or retracted relative to the distal end of the sheath part; and an insulating outer tube, having a lumen extending along an axis of the sheath part, in which the hollow pull rod and the clip component are accommodated; and
the operating part is located at a proximal end of the sheath part and comprises: a high-frequency connector, connected to the electrode via a wire; a component, driving the electrode to move by means of an operating wire; a member driving the hollow pull rod to move; and a liquid inlet, allowing a liquid to flow to the hollow tubular portion of the electrode; and
wherein the treatment part further comprises a second pin shaft, a third pin shaft, a fourth pin shaft, a first jaw arm, a second jaw arm, a third jaw arm, and a fourth jaw arm, wherein the hollow pull rod is movably connected to the third jaw arm and the fourth jaw arm by means of the first pin shaft, the third jaw arm and the first jaw arm are movably connected by the third pin shaft, the fourth jaw arm and the second jaw arm are movably connected by the fourth pin shaft, and the first jaw arm and the second jaw arm are movably connected to the hollow pull rod by means of the second pin shaft.

11. The multifunctional high-frequency electrosurgical knife according to claim 10, wherein the first jaw arm and the third jaw arm, in a form of a hook structure, are movably connected, and the second jaw arm and the fourth jaw arm, in a form of a hook structure, are movably connected.

12. The multifunctional high-frequency electrosurgical knife according to claim 10, wherein when the clip component is in an opened state, the first clamping element and the second clamping element intersect in a cross shape, and the first clamping element and the second clamping element are symmetrically shaped, so as to form a clip portion of the clip component.

13. A multifunctional high-frequency electrosurgical knife comprising:
 a treatment part, a sheath part, and an operating part,
  wherein the treatment part is located at a distal end of the multifunctional high-frequency electrosurgical knife and comprises: an electrode, configured to cut a tissue and inject a liquid, wherein the electrode is able to be pushed out or retracted relative to a distal end of the sheath part and the electrode has a hollow tubular portion extending in an axial direction; and a clip component configured to perform hemostasis of a tissue, wherein the clip component is able to be pushed out or retracted relative to the distal end of the sheath part and the clip component comprises a first clamping element, a second clamping element, and a first pin shaft by which the first clamping element and the second clamping element are connected, wherein the clip component is able to be opened and closed by the first pin shaft being driven;
  the sheath part is located at a proximal end of the treatment part and comprises: a hollow pull rod, wherein the electrode is able to extend distally from its proximal end through an interior of a proximal end of the hollow pull rod, the hollow pull rod is connected to the first clamping element and the second clamping element by means of the first pin shaft, and the hollow pull rod is operable to drive the clip component to be pushed out or retracted relative to the distal end of the sheath part; and an insulating outer tube, having a lumen extending along an axis of the sheath part, in which the hollow pull rod and the clip component are accommodated; and
  the operating part is located at a proximal end of the sheath part and comprises: a high-frequency connector, connected to the electrode via a wire; a component, driving the electrode to move by means of an operating wire; a member, driving the hollow pull rod to move; and a liquid inlet, allowing a liquid to flow to the hollow tubular portion of the electrode; and
  wherein a locking member is provided on an outer surface of the hollow tubular portion of the electrode, and a limit block is provided on an outer wall of the hollow tubular portion, wherein a maximum distance by which the electrode is protruded distally is controlled by cooperation of the limit block with the first pin shaft, and a minimum distance by which the electrode is protruded distally is controlled by cooperation of the locking member, the first clamping element, and the second clamping element.

14. The multifunctional high-frequency electrosurgical knife according to claim 13, wherein the locking member is block-shaped, ring-shaped, or tubular.

15. The multifunctional high-frequency electrosurgical knife according to claim 13, wherein the limit block is block-shaped or ring-shaped.

* * * * *